United States Patent
Long et al.

(10) Patent No.: US 9,902,083 B2
(45) Date of Patent: Feb. 27, 2018

(54) ABSORBENT ARTICLE SUBSTRATE TRIM MATERIAL REMOVAL PROCESS AND APPARATUS

(75) Inventors: Michael Devin Long, Springfield Township, OH (US); Nathan Alan Gill, Cincinnati, OH (US); Andreas Josef Dreher, Clifton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 975 days.

(21) Appl. No.: 12/894,788

(22) Filed: Sep. 30, 2010

(65) Prior Publication Data
US 2012/0079926 A1  Apr. 5, 2012

(51) Int. Cl.
*B26D 7/18* (2006.01)
*B26D 1/26* (2006.01)
(Continued)

(52) U.S. Cl.
CPC .......... *B26D 7/18* (2013.01); *A61F 13/15707* (2013.01); *B26D 3/10* (2013.01); *B26F 1/384* (2013.01); *D06H 7/06* (2013.01); *B26D 7/1854* (2013.01); *B26D 7/1863* (2013.01); *Y10T 83/0467* (2015.04); *Y10T 83/2074* (2015.04); *Y10T 83/4838* (2015.04)

(58) Field of Classification Search
CPC ...... B26D 7/18; B26D 7/1845; B26D 7/1854; B26D 7/1863; B26D 3/10; B26F 3/00; B26F 1/384; B23D 25/00; B23D 25/02; B23D 25/04; B23D 25/12; Y10T 156/1052; Y10T 83/0453; Y10T 83/0467; Y10T 83/483; Y10T 83/4838; Y10T 83/202; Y10T 83/2074; Y10T 83/2083; Y10T 83/2087; Y10T 83/207; Y10T 83/2096; Y10T 83/21; Y10T 83/2179; Y10T 83/2196; Y10T 83/6584; Y10T 83/6585; Y10T 83/6587; Y10T 83/6588; Y10T 83/739; Y10T 83/741; Y10T 83/743; Y10T 83/744; Y10T 83/745; A61F 13/15707; D06H 7/06
USPC ....... 83/24, 27, 343, 346, 78, 102, 105, 107, 83/100, 111, 113, 149, 156, 425, 83/425.1–425.3, 444, 446–449; 156/250, 156/510
See application file for complete search history.

(56) References Cited

U.S. PATENT DOCUMENTS 3,607,578 A   9/1971 Berg et al.
3,680,419 A   8/1972 Stoop
(Continued)

FOREIGN PATENT DOCUMENTS

CN   102152330   11/2012
DE   27 55 648   6/1987
(Continued)

OTHER PUBLICATIONS

PCT International Search Report, dated Mar. 2, 2012, 8 pages.

*Primary Examiner* — Phong Nguyen
(74) *Attorney, Agent, or Firm* — Charles R. Matson

(57) ABSTRACT

Aspects of the present disclosure involve methods and apparatuses for cutting and removing trim from an advancing substrate. Particular embodiments of the apparatuses and methods disclosed herein provide for removal of continuous lengths of trim, and in some embodiments, discrete pieces of trim from an advancing substrate.

15 Claims, 9 Drawing Sheets

(51) Int. Cl.
  *A61F 13/15* (2006.01)
  *B26D 3/10* (2006.01)
  *B26F 1/38* (2006.01)
  *D06H 7/06* (2006.01)

(56) References Cited

U.S. PATENT DOCUMENTS

| | | | |
|---|---|---|---|
| 3,872,752 | A | 3/1975 | Remde et al. |
| 3,949,653 | A | 4/1976 | Schröter |
| 4,274,318 | A | 6/1981 | Passafiume et al. |
| 4,295,842 | A | 10/1981 | Bell |
| 4,329,893 | A | 5/1982 | Wong |
| 4,410,315 | A | 10/1983 | Frye |
| 4,480,516 | A | 11/1984 | Leroy |
| 4,596,546 | A | 6/1986 | Schellenberg |
| 4,599,926 | A | 7/1986 | Carlson, Jr. et al. |
| 4,671,152 | A | 6/1987 | Blümle |
| 4,759,247 | A | 7/1988 | Bell et al. |
| 4,846,030 | A | 7/1989 | McMahon et al. |
| 4,922,775 | A | 5/1990 | Winter |
| 5,036,737 | A | 8/1991 | Glaser |
| 5,103,703 | A | 4/1992 | Littleton |
| 5,109,741 | A | 5/1992 | Fuchs |
| 5,140,880 | A | 8/1992 | Littleton |
| 5,156,075 | A | 10/1992 | Campbell, Jr. et al. |
| 5,224,405 | A | 7/1993 | Pohjola |
| 5,656,285 | A | 8/1997 | Sablotsky et al. |
| 5,879,278 | A | 3/1999 | Cox |
| 6,253,819 | B1 | 7/2001 | Frendle et al. |
| 6,475,325 | B1 | 11/2002 | Parrish et al. |
| 6,482,278 | B1 | 11/2002 | McCabe et al. |
| 6,521,320 | B2 | 2/2003 | McCabe et al. |
| 6,596,108 | B2 | 7/2003 | McCabe |
| 6,602,007 | B1 | 8/2003 | Majus |
| 6,634,269 | B2 | 10/2003 | Eckstein et al. |
| 6,718,855 | B2 | 4/2004 | Kane |
| 6,723,948 | B2 | 4/2004 | Hesterman |
| 6,786,995 | B2 | 9/2004 | Frendle et al. |
| 6,893,528 | B2 | 5/2005 | Middelstadt et al. |
| 6,895,845 | B2 | 5/2005 | Snyder |
| 6,966,245 | B1 | 11/2005 | Simpson |
| 7,323,072 | B2 | 1/2008 | Engelhart et al. |
| 7,533,709 | B2 | 5/2009 | Meyer |
| 7,780,052 | B2 | 8/2010 | McCabe |
| 7,849,772 | B2 | 12/2010 | Monteil |
| 8,007,623 | B2 | 8/2011 | Andrews |
| 8,016,972 | B2 | 9/2011 | Andrews et al. |
| 8,069,894 | B2 | 12/2011 | Yamamoto |
| 8,097,110 | B2 | 1/2012 | Schiebout |
| 8,172,977 | B2 | 5/2012 | McCabe et al. |
| 8,276,638 | B2 | 10/2012 | Yamamoto |
| 8,292,792 | B2 | 10/2012 | Yamamoto |
| 8,293,056 | B2 | 10/2012 | McCabe |
| 8,656,817 | B2 | 2/2014 | Fritz et al. |
| 2004/0007328 | A1* | 1/2004 | Popp et al. ................. 156/494 |
| 2004/0216569 | A1 | 11/2004 | Mizutani et al. |
| 2005/0092146 | A1 | 5/2005 | Carbone, II et al. |
| 2007/0095463 | A1 | 5/2007 | Frendle et al. |
| 2007/0142798 | A1 | 6/2007 | Goodlander et al. |
| 2007/0142806 | A1 | 6/2007 | Roe et al. |
| 2007/0251364 | A1* | 11/2007 | Blumle ................. B26D 7/018 83/100 |
| 2007/0287983 | A1 | 12/2007 | Lodge et al. |
| 2008/0132865 | A1 | 6/2008 | Li et al. |
| 2009/0249931 | A1 | 10/2009 | Grenier et al. |
| 2011/0023671 | A1 | 2/2011 | Herlinger et al. |
| 2012/0234145 | A1 | 9/2012 | Kandermir |
| 2012/0272804 | A1 | 11/2012 | Miyauchi |
| 2013/0075038 | A1 | 3/2013 | McCabe et al. |
| 2013/0160626 | A1 | 6/2013 | Saga |
| 2013/0283987 | A1 | 10/2013 | Pras et al. |

FOREIGN PATENT DOCUMENTS

| | | |
|---|---|---|
| DE | 102005000190 | 6/2007 |
| EP | 0 318 754 A2 | 6/1989 |
| EP | 0 990 588 | 4/2000 |
| EP | 1 302 424 | 12/2006 |
| EP | 2 610 190 | 7/2013 |
| JP | 2000/158389 | 6/2000 |
| JP | 2004/114248 | 4/2004 |
| JP | 2008/237796 | 10/2008 |
| JP | 2011/025321 | 2/2011 |
| JP | 2112/035368 | 2/2012 |
| WO | WO 2009/022053 | 2/2009 |

* cited by examiner

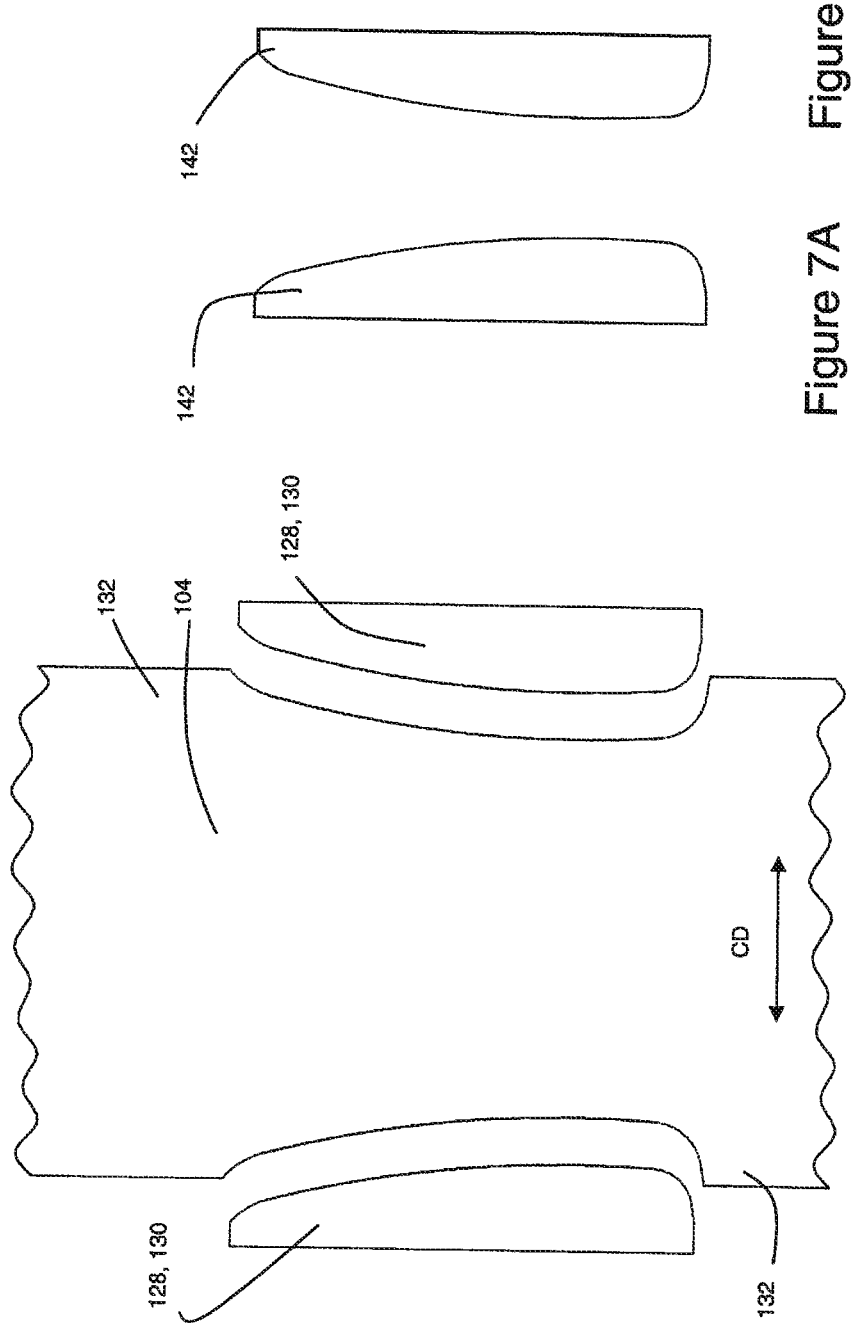

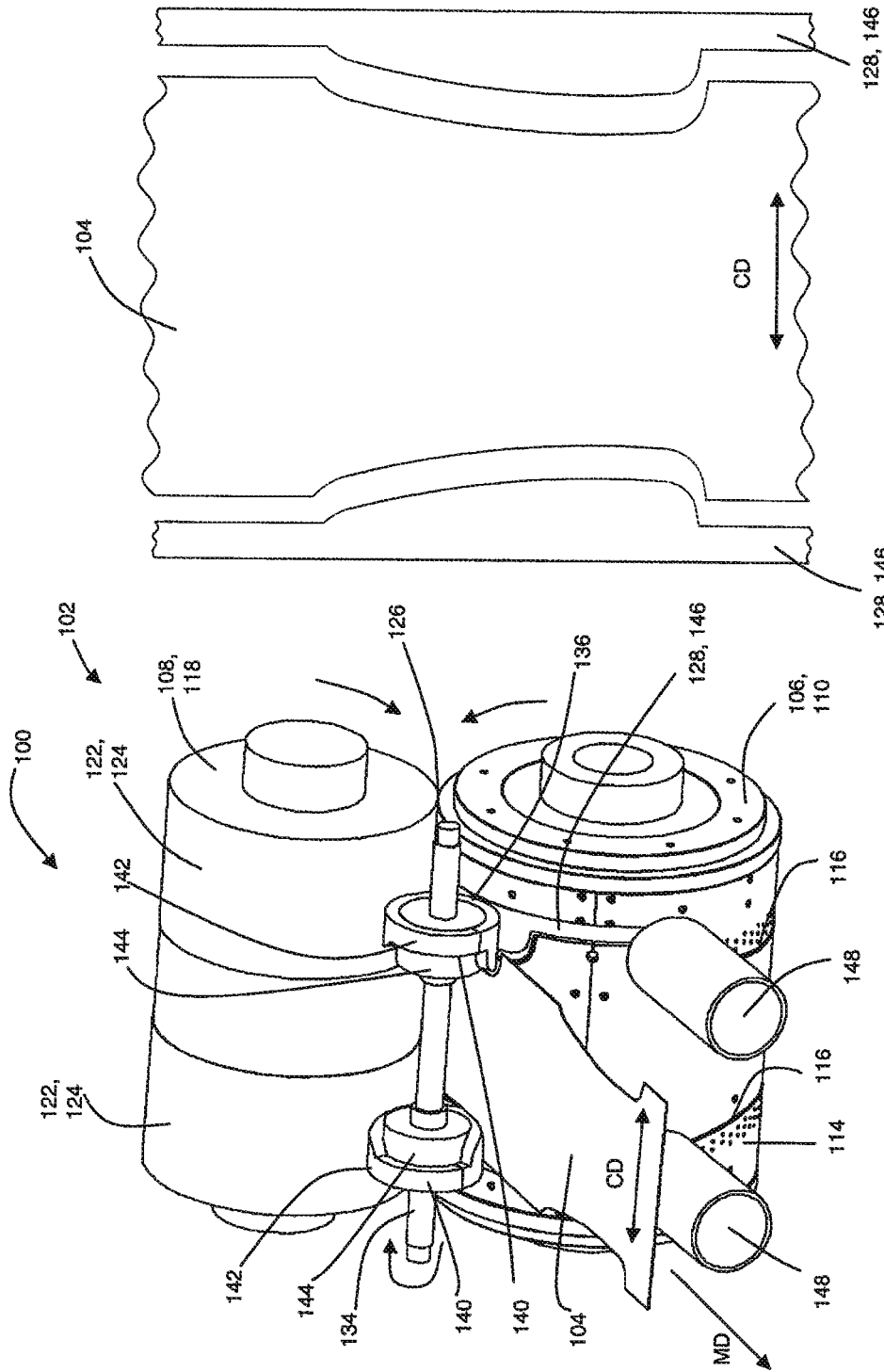

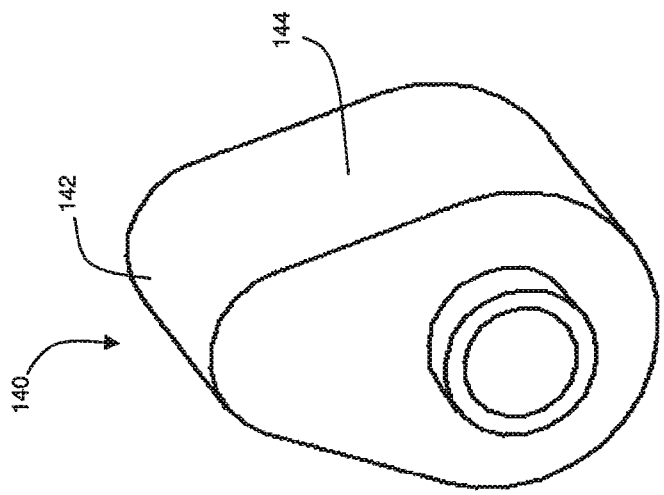
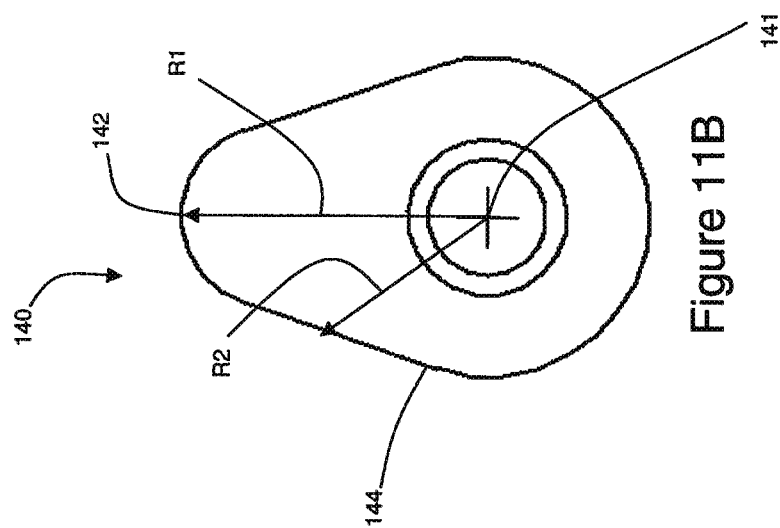

ABSORBENT ARTICLE SUBSTRATE TRIM MATERIAL REMOVAL PROCESS AND APPARATUS

FIELD OF THE INVENTION

The present disclosure relates to methods and apparatuses utilizing continuous substrates for manufacturing articles, and more particularly, methods and apparatuses for removing trim cut from an advancing substrate.

BACKGROUND OF THE INVENTION

Along an assembly line, various types of articles, such as for example, diapers and other absorbent articles, may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheet, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

Various methods and apparatuses may be used for attaching different components to the advancing web and/or otherwise modify the advancing web. Some production operations are configured to advance substrates in a machine direction and cut and/or remove trim from the advancing substrates. In some operations, a substrate may advance through a cutting station that cuts trim from the advancing substrate. The trim may subsequently be diverted from the advancing substrate and machine direction and into a vacuum chute or other similar apparatus for disposal. In some instances after passing through the cutting nip, the trim may remain attached to the advancing substrate by a few uncut fibers after passing through the cutting station. As such, the trim may undesirably continue to advance with the substrate along the assembly line for further processing.

SUMMARY OF THE INVENTION

Aspects of the present disclosure involve methods and apparatuses for cutting and removing trim from an advancing substrate. Particular embodiments of the apparatuses and methods disclosed herein provide for removal of continuous lengths of trim, and in some embodiments, discrete pieces of trim from an advancing substrate.

In one form, an apparatus for cutting and removing trim material from an advancing substrate includes a substrate trimming unit. The substrate trimming unit includes: a first roller adapted to rotate around a first axis of rotation, the first roller having an outer circumferential surface; and a second roller adapted to rotate around a second axis of rotation, the second roller having an outer circumferential surface. The outer circumferential surface of the first roller is in contact with the outer circumferential surface of the second roller to define a first nip between the first roller and the second roller; and the first roller and the second roller rotate in opposite directions to cut trim material from the advancing substrate as the advancing substrate passes through the first nip. The substrate trimming unit also includes a third roller adapted to rotate around a third axis of rotation, the third roller having a first outer circumferential surface and a second outer circumferential surface, wherein the first outer circumferential surface is disposed radially outward from the second outer circumferential surface. The first outer circumferential surface of the third roller is adjacent the outer circumferential surface of the first roller to define a second nip as the third roller and the second roller rotate in opposite directions such that the second nip separates trim material from the advancing substrate.

In another form, a method for cutting and removing trim material from a substrate includes the steps of: rotating a first roller about a first axis of rotation, the first roller having an outer circumferential surface; rotating a second roller about a second axis of rotation, the second roller having an outer circumferential surface, wherein the first roller and the second roller rotate in opposite directions; defining a first nip between the first roller and the second roller; continuously advancing a substrate in a machine direction to the first nip; cutting trim material from the substrate as the substrate advances through the first nip; rotating a third roller about a third axis of rotation, the third roller having a first outer circumferential surface and a second outer circumferential surface, wherein the first outer circumferential surface is disposed radially outward from the second outer circumferential surface, and wherein first outer circumferential surface of the third roller is adjacent the outer circumferential surface of the first roller to define a second nip as the third roller and the first roller rotate in opposite directions; and separating the trim material from the substrate by advancing the trim material through the second nip.

BRIEF DESCRIPTION OF THE DRAWINGS

FIG. 6 is a top side view of a substrate with discrete pieces of trim cut from longitudinal side edge regions of the substrate.

FIG. 7A is a top side view of a first outer circumferential surface of a trim assist roller in a flat configuration.

FIG. 7B is a top side view of a first outer circumferential surface of a trim assist roller in a flat configuration.

FIG. 8 is an isometric view a second embodiment of a substrate trimming and trim removal apparatus a continuous strip of trim material from an advancing substrate.

FIG. 9 is a top side view of a substrate with continuous lengths of trim cut from longitudinal side edge regions of the substrate.

FIG. 11A is a detailed isometric view of an embodiment of a trim removal assist roller.

FIG. 11B is a side view of the trim removal assist roller shown in FIG. 11A.

DETAILED DESCRIPTION OF THE INVENTION

Figure 1:
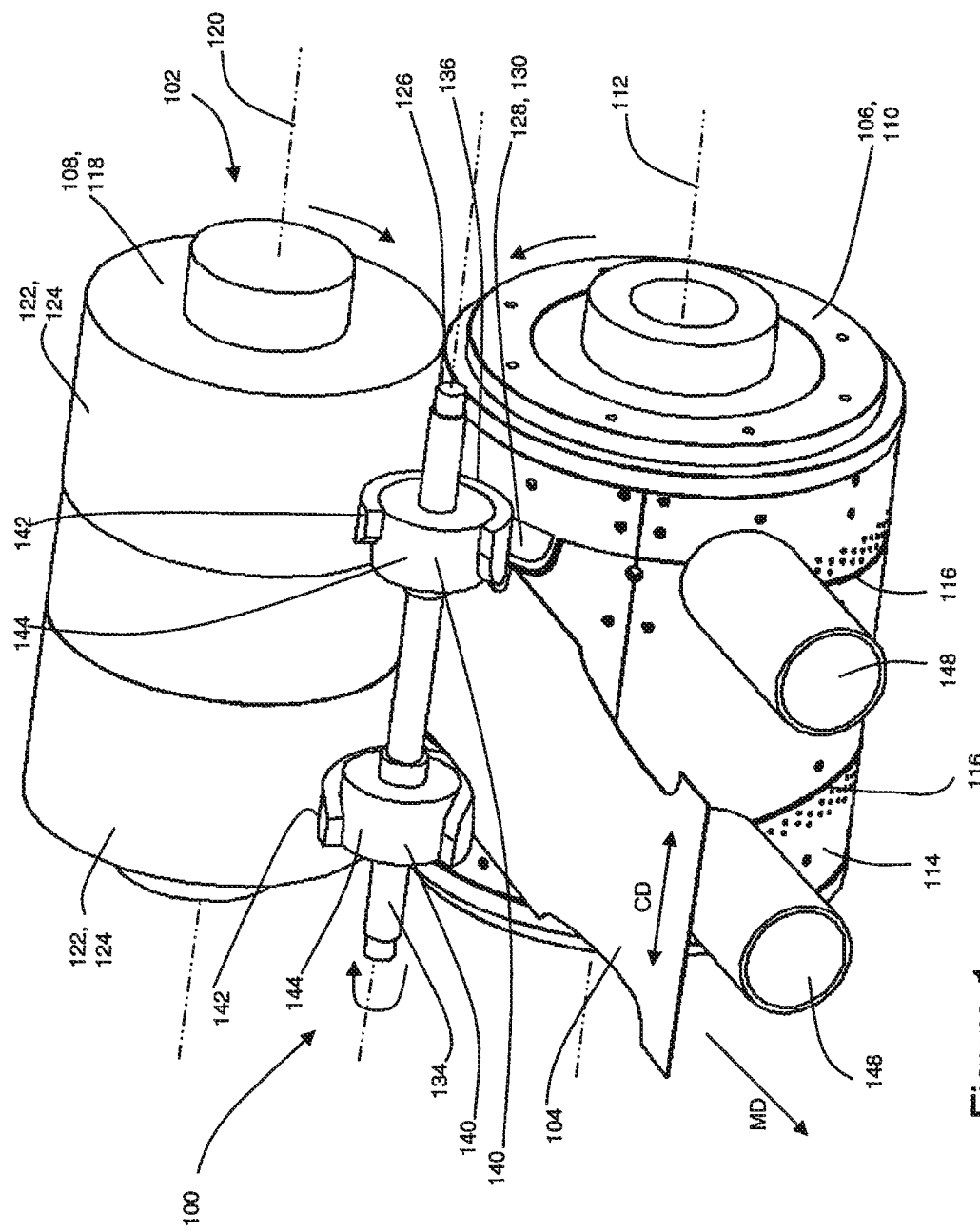
FIG. 1 is an isometric view a first embodiment of a trim removal apparatus removing discrete pieces of trim material from an advancing substrate.

The following term explanations may be useful in understanding the present disclosure:

"Absorbent article" is used herein to refer to consumer products whose primary function is to absorb and retain soils and wastes. Non-limiting examples of incontinent absorbent articles include diapers such as PAMPERS diapers, training and pull-on pants such as PAMPERS FEEL 'N LEARN and EASY UPS, adult incontinence briefs and undergarments such as ATTENDS adult incontinence garments, feminine hygiene garments such as panty liners, absorbent inserts, and the like such as ALWAYS and TAMPAX, all sold by The Procter & Gamble Company.

"Diaper" is used herein to refer to an absorbent article generally worn by infants and incontinent persons about the lower torso.

The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "disposed" is used herein to mean that an element(s) is formed (joined and positioned) in a particular place or position as a macro-unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a layer or layers or fibrous materials, films and foils such as plastic films or metallic foils that may be used alone or laminated to one or more web, layer, film and/or foil. As such, a web is a substrate.

The term "nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The terms "elastic" and "elastomeric" as used herein refer to any material that upon application of a biasing force, can stretch to an elongated length of at least about 110% of its relaxed, original length (i.e. can stretch to 10% more than its original length), without rupture or breakage, and upon release of the applied force, recovers at least about 40% of its elongation. For example, a material that has an initial length of 100 mm can extend at least to 110 mm, and upon removal of the force would retract to a length of 106 mm (40% recovery). The term "inelastic" refers herein to any material that does not fall within the definition of "elastic" above.

The term "extensible" as used herein refers to any material that upon application of a biasing force, can stretch to an elongated length of at least about 110% of its relaxed, original length (i.e. can stretch to 10%), without rupture or breakage, and upon release of the applied force, shows little recovery, less than about 40% of its elongation.

The terms "activating", "activation" or "mechanical activation" refer to the process of making a substrate, or an elastomeric laminate more extensible than it was prior to the process. "Live stretch" includes stretching elastic and bonding the stretched elastic to a substrate. After bonding, the stretched elastic is released causing it to contract, resulting in a "corrugated" substrate. The corrugated substrate can stretch as the corrugated portion is pulled to about the point that the substrate reaches at least one original flat dimension. However, if the substrate is also elastic, then the substrate can stretch beyond the relaxed length of the substrate prior to bonding with the elastic. The elastic is stretched at least 25% of its relaxed length when it is bonded to the substrate.

Aspects of the present disclosure involve methods and apparatuses utilizing continuous substrates for manufacturing articles, and more particularly, methods and apparatuses for cutting and removing trim from an advancing substrate. Particular embodiments of the apparatuses and methods disclosed herein provide for removal of trim, and in some embodiments, discrete pieces of trim from an advancing substrate. It is to be appreciated that the trim removal apparatus and processes disclosed herein may be used to remove continuous lengths of trim as well as discrete pieces of trim cut from an advancing substrate. More particularly, as the substrate advances in the machine direction, the trim removal apparatus and methods herein may be used to separate and remove trim cut from and/or along either or both opposing side edges of the advancing substrate. In addition, the trim removal apparatus and methods herein may be also used to separate and remove trim cut between both opposing side edges of the advancing substrate. It should also be appreciated that the trim may be in the form of a continuous strip of material and/or discrete pieces of material cut from the advancing substrate.

As discussed below in more detail, embodiments of a trim removal apparatus may include a substrate trimming unit including a first roller and a second roller. The first roller may be located adjacent the second roller to define a first nip between the first roller and the second roller. In some embodiments, the first roller may be configured with a pattern knife and the second roller may be configured with an anvil surface. And the outer circumferential surface of the first roller may be in rolling contact with the outer circumferential surface of the second roller. As a substrate advances through the first nip, trim is cut from the advancing substrate. The trim removal apparatus may also include a third roller having a first outer circumferential surface and a second outer circumferential surface, wherein the first outer circumferential surface is disposed radially outward from the second outer circumferential surface. As discussed in more detail below, the third roller may be positioned adjacent the first roller to define a second nip between the second roller and the third roller. In some embodiments, the first outer circumferential surface of the third roller may be in rolling contact with the outer circumferential surface of the first roller. And in other embodiments, a gap may exist between the first outer circumferential surface of the third roller and the outer circumferential surface of the first roller. In some configurations, the second outer circumferential surface may intermittently contact the outer circumferential surface of the first roller as the first and third rollers rotate. In other configurations, the second outer circumferential surface may remain in constant contact with the outer circumferential surface of the first roller as the first and third rollers rotate. In operation, the substrate continues in the machine direction after passing through the first nip while the trim is diverted to advance through the second nip. As such, the second nip helps to separate the trim from the advancing substrate as the trim advances through the second nip.

As mentioned above, apparatuses and methods of the present disclosure may be utilized to remove trim from continuous substrates used in the manufacture of absorbent articles. Such substrates may be utilized in absorbent article components such as, for example: backsheets, topsheets, absorbent cores, front and/or back ears, fastener components, and various types of elastic webs and components such as leg elastics, barrier leg cuff elastics, and waist elastics. Exemplary descriptions of absorbent article components and substrates are provided below with reference to FIG. 13. In addition, substrates may include continuous webs of material and component parts mounted on carrier substrates or may be in the form of a continuous substrate.

Although much of the present disclosure is provided in the context of manufacturing absorbent articles, it is to be appreciated that the apparatuses and methods disclosed herein may be applied to the manufacture of other types of articles and products manufactured from continuous substrates. Examples of other products include absorbent articles for inanimate surfaces such as consumer products whose primary function is to absorb and retain soils and wastes that may be solid or liquid and which are removed from inanimate surfaces such as floors, objects, furniture and the like. Non-limiting examples of absorbent articles for inanimate surfaces include dusting sheets, pre-moistened wipes or pads, pre-moistened cloths, paper towels, dryer sheets and dry-cleaning clothes such. Additional examples of products include absorbent articles for animate surfaces whose primary function is to absorb and contain body exudates and, more specifically, devices which are placed against or in proximity to the body of the user to absorb and contain the various exudates discharged from the body. Non-limiting examples of incontinent absorbent articles include diapers, training and pull-on pants, adult incontinence briefs and undergarments, feminine hygiene garments such as panty liners, absorbent inserts, and the like, toilet paper, tissue paper, facial wipes or clothes, and toilet training wipes. Still other examples of products may include packaging components and substrates and/or containers for laundry detergent and coffee, which may be produced in pellets or pouches and may be manufactured in a converting or web process or even discreet products produced at high speed such as high-speed bottling lines, cosmetics, razor blade cartridges, and disposable consumer batteries.

Figure 3:
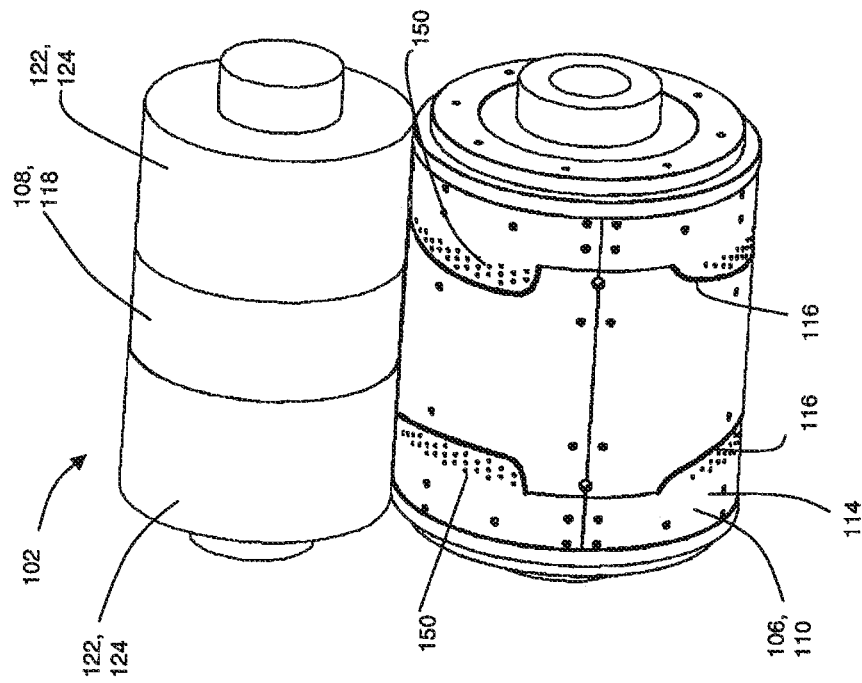
FIG. 3 is an isometric view of a substrate trimming unit shown in FIG. 1.
Figure 2:
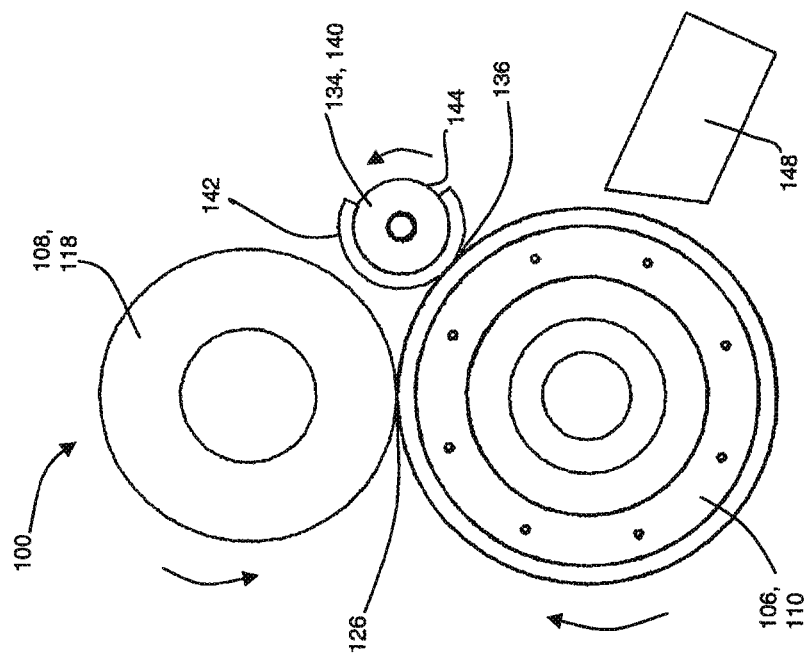
FIG. 2 is a schematic side view of a first embodiment of a substrate trimming and trim removal apparatus.

FIGS. 1 and 2 show an embodiment of a trim removal apparatus 100 including a substrate trimming unit 102 that cuts trim from a substrate 104 advancing in a machine direction MD. More particularly, the substrate trimming unit 102, which is also shown in detail in FIG. 3, includes a first roller 106 and a second roller 108. The first roller 106 is depicted in the form of a die roller 110 adapted to rotate around a first axis of rotation 112 and having an outer circumferential 114 surface including at least one pattern knife 116 protruding therefrom. The second roller 108 is depicted in the form of an anvil roller 118 adapted to rotate around a second axis of rotation 120 and having an outer circumferential surface 122 including a smooth anvil surface 124. A first nip 126 is defined by the outer circumferential surface 114 of the first roller 106 and the outer circumferential surface 114 of the second roller 108. In operation, the first roller 106 and the second roller 108 rotate around the first axis 112 and second axis of rotation 120, respectively, and the substrate 104 advances in a machine direction MD through the first nip 126. The pattern knife 116 presses against the anvil surface 124 and cuts through the substrate 104 as the substrate advances through the first nip 126. As such, the pattern knife 116 cuts trim 128 from the advancing substrate 104. In some embodiments, the pattern knife 116 may be configured to cut trim in the form of discrete pieces 130 from the advancing substrate 104. For example, FIG. 6 shows two discrete pieces 130 of trim 128 cut from opposing longitudinal side edge regions 132 of the substrate 104. Although FIGS. 1-3 show the first roller 106 in the form of a die roller 110 and the second roller 108 in the form of an anvil roller 118, it is to be appreciated that in other embodiments, the first roller 106 may be in the form of an anvil roller and the second roller 110 may be in the form of a die roller.

Figure 5:
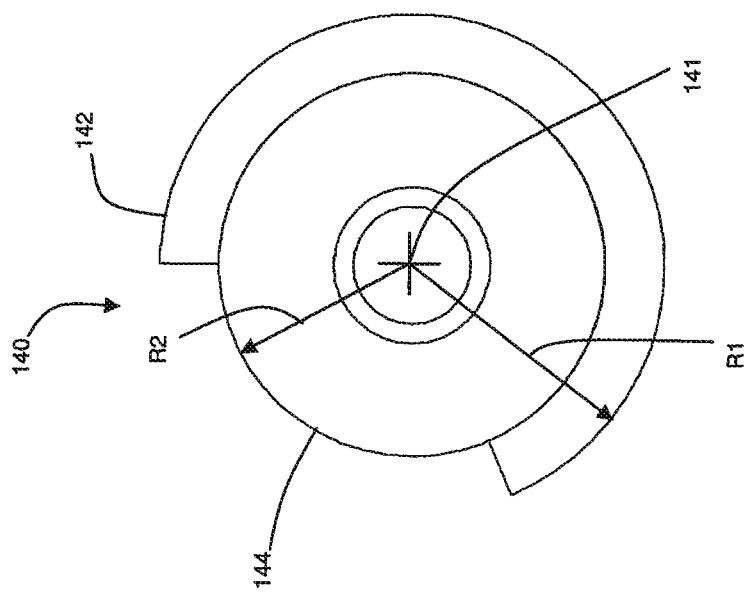
FIG. 5 is a side view of the trim removal assist roller shown in FIG. 4.
Figure 4:
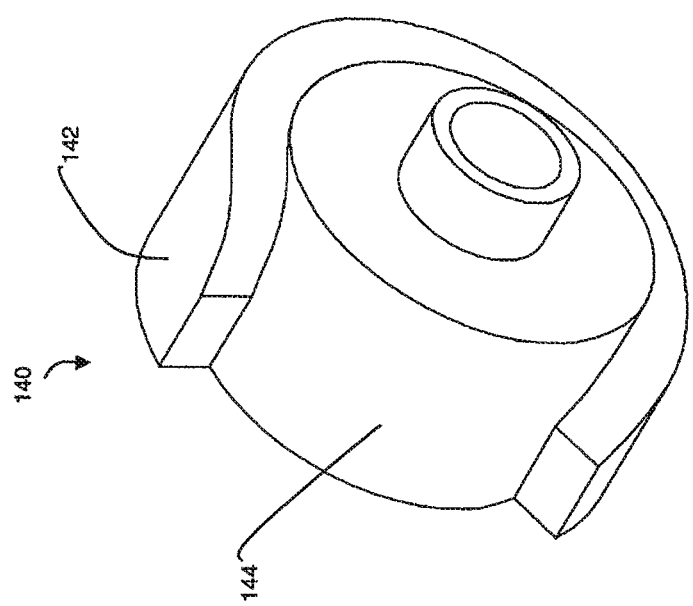
FIG. 4 is a detailed isometric view of an embodiment of a trim removal assist roller.

As shown in FIGS. 1 and 2, the trim removal apparatus 100 may also include a third roller 134 defining a second nip 136 between the first roller 106 and the third roller 134. As shown in FIGS. 1 and 2, the third roller 134 is located adjacent the first roller 106 and is adapted to rotate around a third axis of rotation 138. The third roller 134 includes two trim assist rollers 140. As discussed in more detail below, as the substrate 104 advances from the first nip 126, the trim assist rollers 140 divert and force the trim 128 to pass through the second nip 136 while the remainder of the substrate 104 advances in the machine direction MD. As shown in FIGS. 1, 4, and 5, each trim assist roller 140 includes a first outer circumferential surface 142 and a second outer circumferential surface 144, wherein the first outer circumferential surface 142 is disposed radially outward from the second outer circumferential surface 144. More particularly, the trim assist roller 140 defines a center of rotation 141. And the first circumferential surface 142 is disposed at a radius R1 from the center of rotation 141, and the second circumferential surface 144 is disposed at a radius R2 from the center of rotation 141, wherein R1 is greater than R2. In some embodiments, the first outer circumferential surface 142 of the trim assist roller 140 may be in rolling contact with the outer circumferential. surface 122 of the first roller 106. In other embodiments, the first outer circumferential surface 142 of the trim assist roller 140 may be separated from and define a gap between the outer circumferential surface 122 of the first roller 106. It is to be appreciated that the gap may be configured to define various distances, such as for example, the caliper of the substrate 104.

As previously mentioned, the trim removal apparatus 100 may be configured to remove discrete pieces 130 of trim 128 from an advancing substrate 104. In other embodiments, the trim removal apparatus 100 may be configured to remove a continuous length of trim from a substrate. For example, as shown in FIG. 8, the first and second rollers 106, 108 may be configured to cut continuous lengths 146 of trim 128 from a substrate 104 advancing in the machine direction MD. FIG. 9 shows two continuous lengths 146 of trim 128 cut from opposing longitudinal side edge regions 132 of the substrate 104. In addition, the first circumferential surfaces 142 of the trim assist rollers 140 are adapted to engage and divert the continuous lengths of trim through the second nip 136. It is also to be appreciated that the trim removal apparatus 100 can be configured to remove various types of trim, both continuous and discrete pieces and combinations thereof, as well as trim cut from various different locations on the advancing substrate. For example, the trim removal apparatus can be configured to remove one more discrete pieces of trim cut from a center portion of the substrate.

The trim removal apparatus 100 may include other features to aid in trim separation and removal from an advancing substrate 104. For example, as shown in FIGS. 1 and 8, embodiments of the trim removal apparatus 100 may include a vacuum chute 148 located near the second nip 136 that accepts removed trim 128 for disposal. Also shown in FIGS. 1 and 8, the first roller 106 may include a vacuum imposed through vacuum ports 150 in the outer circumferential surface 122 of the first roller 106. The vacuum may operate to help hold the trim 128 against the outer circumferential surface 122 of the first roller 106. In such a configuration, the vacuum may also be configured to operate intermittently as the first roller 106 rotates such that the vacuum operates to hold the trim 128 against the outer circumferential surface 122 of the first roller 106 while advancing between the first nip 126 and the second nip 136 and then ceases operation to release the trim 128 from the first roller 106 after the passing through the second nip 136. The first roller 106 may also be configured to discharge air through the ports 150 in the outer circumferential surface 122 to "blow-off" or remove the trim 128 from the outer circumferential surface of the first roller 106 after passing through the second nip 126. In some embodiments, the ports 150 in the outer circumferential surface of the first roller 106 are arranged in a pattern that substantially matches the shape of the trim 128 being removed.

It is to be appreciated that the trim assist roller 140 may be configured in various different ways and may have various shapes and sizes. For example, the first circumferential surface 142 of the trim assist roller 140 may be configured to have various shapes and sizes. In some embodiments, the first circumferential surface 142 may define a shape that corresponds with and/or matches the shape the trim 128 cut from the substrate 104. For example, the first circumferential surfaces 142 of the trim assist rollers 140 in FIG. 1 may define shapes that correspond with the shapes of the discrete pieces 130 of trim 128 shown in FIG. 6. FIGS. 7A and 7B show first circumferential surfaces 142 of the trim assist roller 140 in a flat configuration to illustrate how the shapes correspond with the shapes of the discrete pieces 130 of trim 128 shown in FIG. 6. In another example, the first circumferential surfaces 142 of the trim assist rollers 140 such as shown in FIG. 8 may define shapes that correspond with the shapes of the continuous lengths 146 of trim 128 shown in FIG. 9.

Figure 10A:
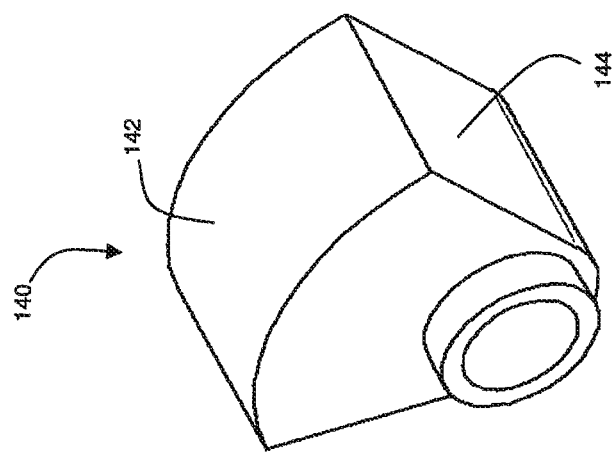
FIG. 10A is a detailed isometric view of an embodiment of a trim removal assist roller.
Figure 10B:
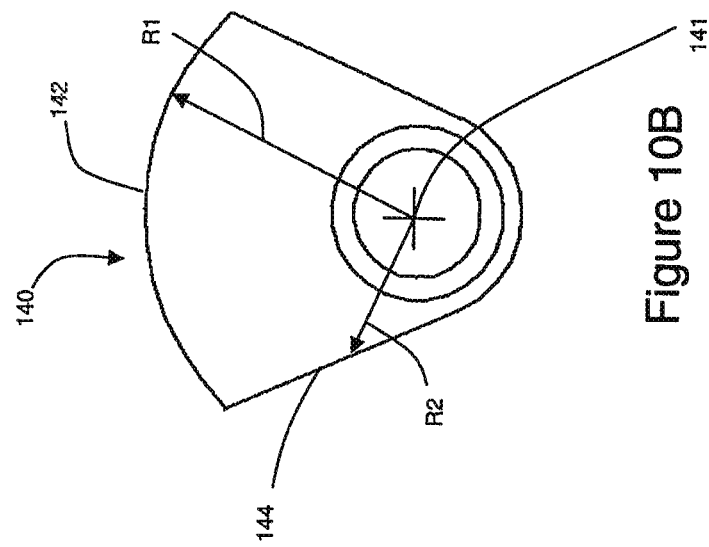
FIG. 10B is a side view of the trim removal assist roller shown in FIG. 10A.

In still another example, FIGS. 10A and 10B show a trim assist roller 140 configured with a first circumferential surface 142 at a constant radial distance R1 from the center of rotation 141, and having a second circumferential surface 144 at a varying radial distance R2 from the center of rotation 141. In yet another example, FIGS. 11A and 11B show a trim assist roller 140 configured with a first circumferential surface 142 at a constant radial distance R1 from the center of rotation 141, and having a second circumferential surface 144 at a varying radial distance R2 from the center of rotation 141. In addition, the first circumferential surface 142 on the trim assist roller 140 of FIGS. 11A and 11B is defined by a line, as opposed to a two-dimensional area having a length and a width.

In some embodiments, the trim assist roller 140 may be configured with a first circumferential surface 142 that is integral with the roller, wherein the trim assist roller is molded or solid machine. In some embodiments, the trim assist roller 140 may be constructed as a muli-piece structure. It is also to be appreciated that the trim assist roller 140 can be configured to rotate at a constant speed or a variable speed.

To provide additional context to the above discussion, the following provides a general description of an example implementation of the trim removal apparatuses and processes herein. With reference to FIGS. 1-11B, a substrate advances 104 in the MD through the first nip 126 between the rotating first roller 106 and second roller 108. And the engagement of the pattern knife 116 on the first roller 106 with the anvil surface 124 on the second roller 108 cuts trim 128 from the substrate 104. As discussed above, the trim 128 may be cut in discrete pieces 130 and/or continuous lengths 146. As the substrate 104 advances from the first nip 126, the third roller 134 engages the trim 128 to help separate the trim from the substrate. More particularly, as the substrate 104 continues to advance in the machine direction MD, the first circumferential surfaces 142 of the trim assist rollers 140 engage the trim 128 and divert the trim into the second nips 136 between the trim assist rollers 140 and the first roller 106. As such, engagement of the trim 128 with the first circumferential surfaces 142 of the trim assist rollers 140 help to ensure that the trim is separated from the advancing substrate 104 that might otherwise be attached via a few uncut fibers. The trim 128 may subsequently be diverted from the advancing substrate 104 and into a vacuum chute 148 or other similar apparatus for disposal.

Figure 12:
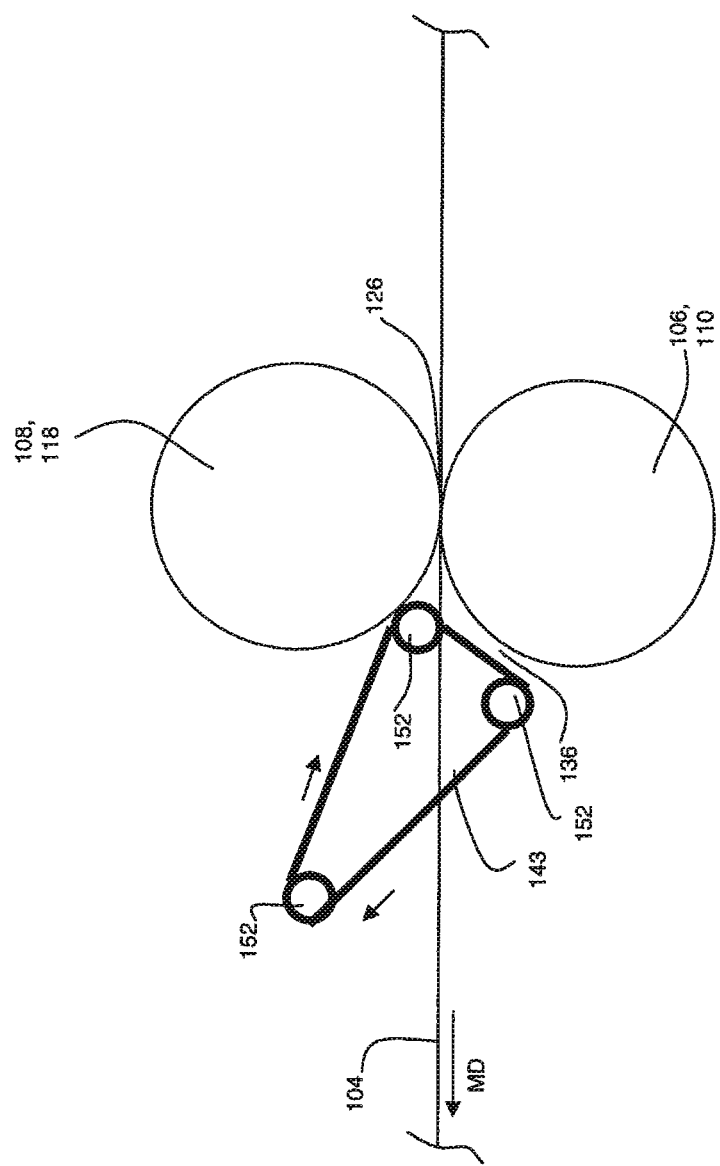
FIG. 12 shows a schematic side view of a substrate trimming and trim removal apparatus including a trim removal belt.

FIG. 12 shows yet another configuration that utilizes a trim assist belt 143 instead of a trim assist roller. In particular, the trim assist belt 143 may be configured as an endless belt supported by two or more rollers 152. As shown in FIGS. 1 and 2, the trim removal apparatus 100 may also include a third roller 134 defining a second nip 136 between the first roller 106 and the third roller 134. As shown in FIGS. 1 and 2, the third roller 134 is located adjacent the first roller 106 and is adapted to rotate around a third axis of rotation 138. As the substrate 104 advances from the first nip 126, the trim assist belt 142 diverts and force the trim 128 to pass through the second nip 136 while the remainder of the substrate 104 advances in the machine direction MD. In some embodiments, the trim assist belt 143 may be in contact with the outer circumferential surface 122 of the first roller 106. In other embodiments, the trim assist belt 143 may be separated from and define a gap between the outer circumferential surface 122 of the first roller 106. It is to be appreciated that the gap may be configured to define various distances, such as for example, the caliper of the substrate 104. As discussed above with reference to the first circumferential surfaces 142 of the trim assist roller 140, the trim assist belt 143 may define a shape that corresponds with the shape of the trim.

Figure 13:
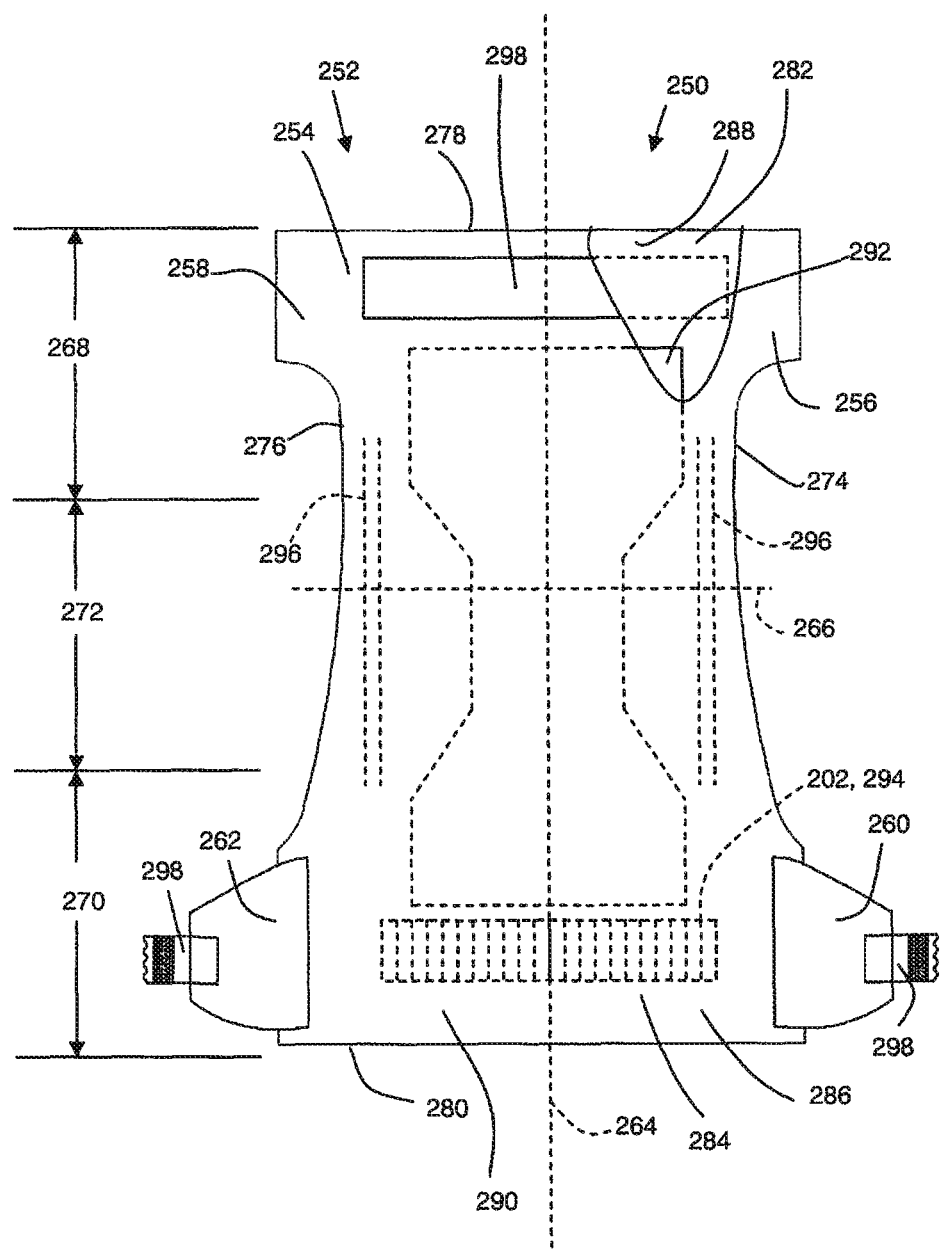
FIG. 13 is a top plan view of a disposable absorbent article.

As previously mentioned, the apparatuses and methods herein may be used to provide for the cutting and removal of trim material from advancing substrates and components during the manufacture of various different products. For the purposes of a specific illustration, FIG. 13 shows one example of a disposable absorbent article 250, such as described in U.S. Patent Publication No. US2008/0132865 A1, in the form of a diaper 252 that may be constructed from such substrates and components manipulated during manufacture according to the apparatuses and methods disclosed herein. In particular, FIG. 13 is a plan view of one embodiment of a diaper 252 including a chassis 254 shown in a flat, unfolded condition, with the portion of the diaper 252 that faces away from the wearer oriented towards the viewer. A portion of the chassis structure is cut-away in FIG. 13 to more clearly show the construction of and various features that may be included in embodiments of the diaper.

As shown in FIG. 13, the diaper 252 includes a chassis 254 having a first ear 256, a second ear 258, a third ear 260, and a fourth ear 262. To provide a frame of reference for the present discussion, the chassis is shown with a longitudinal axis 264 and a lateral axis 266. The chassis 254 is shown as having a first waist region 268, a second waist region 270, and a crotch region 272 disposed intermediate the first and second waist regions. The periphery of the diaper is defined by a pair of longitudinally extending side edges 274, 276; a first outer edge 278 extending laterally adjacent the first waist region 268; and a second outer edge 280 extending laterally adjacent the second waist region 270. As shown in FIG. 13, the chassis 254 includes an inner, body-facing surface 282, and an outer, garment-facing surface 284. A portion of the chassis structure is cut-away in FIG. 13 to more clearly show the construction of and various features that may be included in the diaper. As shown in FIG. 13, the chassis 254 of the diaper 252 may include an outer covering layer 286 including a topsheet 288 and a backsheet 290. An absorbent core 292 may be disposed between a portion of the topsheet 288 and the backsheet 290. As discussed in more detail below, any one or more of the regions may be stretchable and may include an elastomeric material or laminate as described herein. As such, the diaper 252 may be configured to adapt to a specific wearer's anatomy upon application and to maintain coordination with the wearer's anatomy during wear.

The absorbent article may also include an elastic waist feature 202 shown in FIG. 13 in the form of a waist band 294 and may provide improved fit and waste containment. The elastic waist feature 202 may be configured to elastically expand and contract to dynamically fit the wearer's waist. The elastic waist feature 202 can be incorporated into the diaper in accordance with the methods discussed herein and may extend at least longitudinally outwardly from the absorbent core 292 and generally form at least a portion of the first and/or second outer edges 278, 280 of the diaper 252. In addition, the elastic waist feature may extend laterally to include the ears. While the elastic waist feature 202 or any constituent elements thereof may comprise one or more separate elements affixed to the diaper, the elastic waist feature may be constructed as an extension of other elements of the diaper, such as the backsheet 290, the topsheet 288, or both the backsheet and the topsheet. In addition, the elastic waist feature 202 may be disposed on the outer, garment-facing surface 284 of the chassis 254; the inner, body-facing surface 282; or between the inner and outer facing surfaces.

The elastic waist feature 202 may be constructed in a number of different configurations including those described in U.S. Patent Publication Nos. US2007/0142806A1; US2007/0142798A1; and US2007/0287983A1, all of which are hereby incorporated by reference herein.

As shown in FIG. 13, the diaper 252 may include leg cuffs 296 that may provide improved containment of liquids and other body exudates. In particular, elastic gasketing leg cuffs can provide a sealing effect around the wearer's thighs to prevent leakage. It is to be appreciated that when the diaper is worn, the leg cuffs may be placed in contact with the wearer's thighs, and the extent of that contact and contact pressure may be determined in part by the orientation of diaper on the body of the wearer. The leg cuffs 296 may be disposed in various ways on the diaper 202.

The diaper 252 may be provided in the form of a pant-type diaper or may alternatively be provided with a re-closable fastening system, which may include fastener elements in various locations to help secure the diaper in position on the wearer. For example, fastener elements 298 may be located on the first and second ears and may be adapted to releasably connect with one or more corresponding fastening elements located in the first or second waist regions. It is to be appreciated that various types of fastening elements may be used with the diaper.

It is to be appreciated that the apparatuses and methods herein may be used to provide for the cutting and removal of trim material from advancing substrates and components during the manufacture of absorbent articles, such as the diaper of FIG. 13. For example, the trim removal apparatus may be used to remove trim material during the manufacture of a topsheet, a backsheet, an absorbent core, an ear, and fastening elements.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for cutting and removing trim material from an advancing substrate, the apparatus comprising:
   a substrate trimming unit comprising:
   a first roller adapted to rotate around a first axis of rotation, the first roller having an outer circumferential surface;

a second roller adapted to rotate around a second axis of rotation, the second roller having an outer circumferential surface; and wherein the outer circumferential surface of the first roller is in contact with the outer circumferential surface of the second roller to define a first nip between the first roller and the second roller; and wherein the first roller and the second roller rotate in opposite directions to cut trim material from the advancing substrate as the advancing substrate passes through the first nip;

a third roller adapted to rotate at a constant speed around a third axis of rotation, the third roller having a first outer circumferential surface and a second outer circumferential surface, wherein the first outer circumferential surface is disposed radially outward from the second outer circumferential surface; and wherein the first outer circumferential surface of the third roller is adjacent the outer circumferential surface of the first roller to define a second nip as the third roller and the first roller rotate in opposite directions such that the first outer circumferential surface diverts the trim material from the advancing substrate and forces the trim material to pass through the second nip to separate the trim material from the advancing substrate.

2. The apparatus of claim 1, wherein the first outer circumferential surface of the third roller intermittently contacts the outer circumferential surface of the first roller as the third roller and the first roller rotate in opposite directions.

3. The apparatus of claim 1, wherein the second roller comprises an anvil roller.

4. The apparatus of claim 3, wherein the first roller includes a vacuum.

5. The apparatus of claim 1, wherein the first roller comprises a die roller.

6. The apparatus of claim 1, wherein the substrate trimming unit is adapted to cut discrete pieces of trim material from the advancing substrate.

7. The apparatus of claim 1, wherein the first outer circumferential surface of the third roller defines a shape substantially similar to shapes defined by the pieces of trim material.

8. The apparatus of claim 1, wherein the substrate trimming unit is adapted to cut a continuous strip of trim material from the advancing substrate.

9. A method for cutting and removing trim material from a substrate, the method comprising the steps of:

rotating a first roller about a first axis of rotation, the first roller having an outer circumferential surface;

rotating a second roller about a second axis of rotation, the second roller having an outer circumferential surface, wherein the first roller and the second roller rotate in opposite directions;

defining a first nip between the first roller and the second roller;

continuously advancing a substrate in a machine direction to the first nip;

cutting trim material from the substrate as the substrate advances through the first nip;

rotating a third roller about a third axis of rotation at a constant speed, the third roller having a first outer circumferential surface and a second outer circumferential surface, wherein the first outer circumferential surface is disposed radially outward from the second outer circumferential surface, and wherein the first outer circumferential surface of the third roller is adjacent the outer circumferential surface of the first roller to define a second nip as the third roller and the first roller rotate in opposite directions; and separating the trim material from the substrate by diverting trim material from the substrate by forcing the trim material through the second nip with the first outer circumferential surface while a remainder of the substrate continues to advance in the machine direction.

10. The method of claim 9, wherein the step of cutting trim material further comprises cutting discrete pieces of trim material from the substrate as the substrate advances through the first nip.

11. The method of claim 9, wherein first outer circumferential surface of the third roller intermittently contacts the outer circumferential surface of the first roller as the third roller and the second roller rotate.

12. The method of claim 9, wherein the second roller comprises an anvil roller.

13. The method of claim 9, wherein the first roller comprises a die roller.

14. The method of claim 9, further comprising the step of holding the discrete pieces of trim material on the outer circumferential surface of the first roller with a vacuum.

15. The method of claim 9, wherein the first outer circumferential surface of the third roller defines a shape substantially similar to shapes defined by the pieces of trim material.

* * * * *